United States Patent [19]

Bernheim et al.

[11] Patent Number: 4,623,428

[45] Date of Patent: Nov. 18, 1986

[54] PROCESS FOR SIZING PAPER WITH ANIONIC HYDROPHOBIC SIZING AGENTS AND CATIONIC RETENTION AIDS

[75] Inventors: Michael Bernheim, Arlesheim; Hubert Meindl, Riehen; Peter Rohringer, Schönenbuch; Hans Wegmüller, Riehen; Dieter Werthemann, Basel, all of Switzerland

[73] Assignee: Ciba-Geigy Corporation, Ardsley, N.Y.

[21] Appl. No.: 663,740

[22] Filed: Oct. 22, 1984

[30] Foreign Application Priority Data

Oct. 27, 1983 [CH] Switzerland .................. 5819/83

[51] Int. Cl.$^4$ .............................. D21H 3/12
[52] U.S. Cl. ................. 162/158; 162/164.1; 162/168.1; 162/175; 162/179
[58] Field of Search ............ 162/158, 179, 164.5, 162/168.5, 168.6, 164.1, 168.1, 175; 8/181, 189, 192, 193, 194

[56] References Cited

U.S. PATENT DOCUMENTS

| | | | |
|---|---|---|---|
| 3,050,437 | 8/1962 | Arlt | 162/158 |
| 3,084,092 | 4/1963 | Arlt, Jr. | 162/158 |
| 3,330,848 | 7/1967 | Ulrich | 260/453 |
| 3,345,251 | 10/1967 | Gaertner | 162/158 |
| 3,454,606 | 7/1969 | Brotherton et al. | 260/397.7 |
| 3,491,064 | 1/1970 | Enders et al. | |
| 3,576,712 | 4/1971 | Hine, Jr. et al. | 162/158 |
| 3,700,623 | 10/1972 | Kelm et al. | |
| 4,729,794 | 7/1981 | Dumas | |

FOREIGN PATENT DOCUMENTS

| | | |
|---|---|---|
| 931887 | 7/1949 | Fed. Rep. of Germany . |
| 865727 | 4/1961 | United Kingdom . |
| 1043437 | 9/1966 | United Kingdom . |
| 1125486 | 8/1968 | United Kingdom . |
| 1318244 | 5/1973 | United Kingdom . |
| 1533434 | 11/1978 | United Kingdom . |

Primary Examiner—Peter Chin
Attorney, Agent, or Firm—Edward McC. Roberts; Kevin T. Mansfield

[57] ABSTRACT

Sizing agents, which are novel compounds and contain at least one anionic or acidic sulfonylcarbonylimide group which may be in salt form and at least two hydrophobic substituents of which at least two are linked to each other through a bridge member of the formula $-CO-NH-A_1-(SO_2-NH-CO)_t$, where $A_1$ is a divalent or trivalent aliphatic, cycloaliphatic or aromatic radical of up to 10 carbon atoms, and t is 1 or 2, are particularly suitable, together with commercially available retention aids, for use in a process for sizing paper or cardboard.

9 Claims, No Drawings

PROCESS FOR SIZING PAPER WITH ANIONIC HYDROPHOBIC SIZING AGENTS AND CATIONIC RETENTION AIDS

The present invention has for its object to provide the paper manufacturer with readily accessible sizing agents which are obtainable in simple manner and, when combined in a novel manner with conventional cationic retention aids, are able to effect good sizing in the manufacture of paper from fibre suspensions.

This object is achieved in the practice of this invention by using the paper manufacture involving the concurrent use of polymeric cationic retention aids sizing agents which contain at least two long chain hydrophobic substituents and at least one anionic or acidic group which is free or in the form of a salt, said hydrophobic substituents being linked through one or more bridge members which contain at least one carbon atom and at least two hetero atoms in the main chain.

Accordingly, the present invention relates to a process for sizing paper or cardboard, which comprises adding, in any order or simultaneously, to an aqueous cellulose-containing fibre suspension which optionally contains fillers, at least (A) one sizing agent which contains 1 or 2 anionic or acidic sulfonylcarbonylimide groups (—$SO_2$—NH—CO—) which are free or in the form of a salt and 2 to 6 hydrophobic substituents each containing at least 5 carbon atoms and at least one of which hydrophobic substituents contains at least 8 carbon atoms and at least two of which hydrophobic substituents are linked to each other through a bridge member of the formula

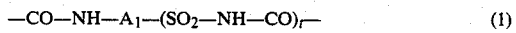

$$-CO-NH-A_1-(SO_2-NH-CO)_t- \quad (1)$$

wherein $A_1$ is a divalent or trivalent aliphatic, cycloaliphatic or aromatic radical of up to 10 carbon atoms and t is 1 or 2, and (B) one polymeric cationic retention aid.

Further objects of the invention are:

the aqueous compositions for carrying out the paper sizing process, which compositions contain, if the sizing agent (A) and the retention aid (B) are added separately to the fibre suspension in any order, only the sizing agent (A) which is at least partly in salt form, together with optional customary auxiliaries, or, if the sizing agent (A) and the retention aid (B) are added to the fibre suspension simultaneously, both the sizing agent (A) which may be at least partly in salt form and the retention aid (B), together with optional customary auxiliaries, the paper or cardboard sized by the process of the present invention, and the use of the sizing agent (A) of the indicated kind for sizing paper or cardboard.

The sizing agents (A) are novel compounds which, together with the process for their preparation, likewise constitute further objects of the present invention.

As salient feature, the sizing agents (A) generally contain 1 or 2 potentially anionic groups which are usually in the form of acidic sulfonylcarbonylimide groups (—$SO_2$—NH—CO—). Sizing agents which contain only one such potentially anionic group are preferred. These potentially anionic groups are able to form anions in aqueous medium at the pH values which the fibre suspensions ordinarily have in paper manufacture. Under the indicated conditions, the cationic retention aids (B) can also alternatively form cations. The ability of the sizing agents to form anions and of the retention aids to form cations under the conditions of paper manufacture can also be termed anionic and cationic respectively. Thus the sizing agents and the retention aids can also be termed anionic sizing agents and cationic retention aids.

The sizing agents (A) are also characterised by the fact that they contain 2 to 6, preferably 2 to 4, hydrophobic substituents having not less than 5, preferably 8 to 22 and, most preferably, 16 to 20 carbon atoms. Examples of such substituents are $C_5$-$C_{12}$cycloalkyl, $C_6$-$C_{10}$aryl, $C_6$-$C_{10}$alkaryl or $C_6$-$C_{10}$aralkyl radicals. Preferred hydrophobic substituents, however, contain unsubstituted phenyl radicals or $C_1$-$C_4$alkyl-substituted phenyl radicals, preferably alkyl or alkenyl radicals which are normally derived from unsaturated or saturated fatty acids, fatty alcohols or fatty amines of at least 6 carbon atoms, preferably of 8 to 22 and, most preferably, 16 to 20 carbon atoms. The hydrophobic substituents contain one or more radicals which consist only of carbon and hydrogen, e.g. cycloalkyl, aryl, alkaryl, aralkyl, alkyl or alkenyl radicals of the indicated kind through which the hydrophobic substituents are linked to the bridge member of the formula (1). These additional divalent or polyvalent radicals consist of a divalent oxygen atom, a secondary or tertiary amino radical, an alkylenediamine radical or a polyalkylenepolyamino radical.

The manner in which the hydrophobic substituents are linked to one another is a further characteristic of the sizing agent (A). The bridge members through which at least two of the hydrophobic substituents are linked correspond to formula (1) above and carry preferably 1 to 13, in particular 1 to 10, carbon atoms, and at least 2 nitrogen atoms and 1 sulfur atom as hetero atoms in the main chain, preferably 1 or 2 sulfur atoms and 2 or 3 nitrogen atoms.

If t in formula (1) is 2, the radical $A_1$ of the bridge member is trivalent. However, divalent radicals $A_1$ of the bridge members of the formula (1), wherein t is 1, are preferred. Suitable radicals $A_1$ are divalent or trivalent, branched or preferably straight chain alkyl radicals of 2 to 10, preferably 2 to 6, carbon atoms, divalent or trivalent cyclopentyl radicals, preferably cyclohexyl radicals, ethyl- or methyl-substituted, but preferably unsubstituted, divalent or trivalent phenyl radicals, and divalent or trivalent dihydronaphthalene, tetrahydronaphthalene, decaline, preferably naphthalene radicals.

In their preferred embodiment, preferred sizing agents accordingly contain one acid sulfonylcarbonylimide group and 2 to 4 hydrophobic substituents, each containing 8 to 22 carbon atoms of the aforementioned kind, at least two of which hydrophobic substituents are linked through a bridge member of the formula

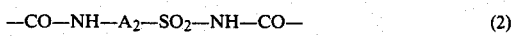

$$-CO-NH-A_2-SO_2-NH-CO- \quad (2)$$

wherein $A_2$ is cycloalkylene, naphthylene, in particular methyl-substituted phenylene, preferably toluylene and xylylene, in particular unsubstituted phenylene or alkylene of 2 to 6 carbon atoms.

Preferred meanings for $A_2$ in formula (2) are isopropylene, propylene, xylylene, toluylene, preferably ethylene and m-phenylene and, in particular, p-phenylene.

Preferred sizing agents (A) are in particular those which are obtainable by chemical reaction of at least (a) 1 mole of a compound of the formula $$O=C=N-A_1-(SO_2-N=C=O)_t \qquad (3)$$

wherein $A_1$ and t have the given meanings, with (b) $t+1$ moles of a fatty alcohol, of a primary or secondary fatty amine and/or of a condensate of a fatty acid and an alkylenediamine or polyalkylenepolyamine, which condensate contains at least one free amino group.

The di- or monosulfonylisocyanates of the formula (3) as component (a) from which the sizing agents (A) are obtainable are known per se, e.g. from U.S. Pat. Nos. 3,454,606 and 3,330,848, and are obtained by known methods. Monosulfonylisocyanates are preferred to disulfoisocyanates as component (a) and have the formula $$O=C=N-A_2-SO_2-N=C=O \qquad (4)$$

wherein $A_2$ has the given meanings.

Component (b), from which the sizing agent (A) is obtainable, is in particular an unsaturated, but preferably a saturated, aliphatic fatty alcohol of 6 to 22, preferably 8 to 22 and, most preferably, 16 to 20 carbon atoms. If component (b) is a fatty amine, it is in general a mono- or dialkylamine or mono- or dialkenylamine, each containing 6 to 22, preferably 8 to 22 and, most preferably, 16 to 20 carbon atoms in the alkyl or alkenyl moiety. Mono- or dialkylamines are preferred to mono- or dialkenylamines as fatty amines. Specific representatives of $C_6$–$C_{20}$ fatty alcohols and of mono- or dialkylamines containing $C_{16}$–$C_{20}$ alkyl radicals as component (b) are, on account of their ready accessibility, hexadecanol, octadecanol, oleyl alcohol, octadecylamine and dioctylamine. Also suitable are technical mixtures of fatty alcohols or fatty amines of the indicated kind.

The fatty alcohols and fatty amines of the aforementioned kind which are suitable for use as component (b) are derived structurally from unsaturated or saturated fatty acids of 6 to 22, preferably 8 to 22 and, most preferably, 16 to 20 carbon atoms. Such acids are for example capronic acid, preferably caprylic acid, lauric acid, myristic or myristoleic acid, palmitoleic acid, oleostearic acid, clupadonic acid, in particular oleic acid, elaidic acid, erucic acid, linolic acid and linoleic acid. Palmitic, stearic, oleic and behenic acid are particularly important, with palmitic and stearic acid being preferred. Also suitable are fatty alcohols and fatty amines which are derived from technical, readily accessible mixtures of the above acids. Synthetic fatty alcohols which are prepared e.g. by oxosynthesis also fall within the above definition.

If component (b), from which the sizing agent (A) is obtainable in a further embodiment of the invention, is a condensate of fatty acids and alkylenediamines or polyalkylenepolyamines, said condensate contains a free amino group, as already mentioned. The fatty acids, or technical mixtures of fatty acids of the indicated kind, are preferred starting components for the preparation of such condensates.

In their preferred embodiment, the alkylenediamines or polyalkylenepolyamines employed as starting components for the preparation of the condensates have the formula $$H_2-N-D_1-(NH-D_2)_{n-1}-NH_2 \qquad (5)$$

wherein $D_1$ and $D_2$ are different or preferably identical and are each propylene or, preferably, ethylene, and n is an integer from 1 to 5, preferably 1, 2, or 3, most preferably 2. Examples of specific representatives are tetraethylenepentamine, triethylenetetramine, preferably ethylenediamine and, most preferably, diethylenetriamine.

As the condensate must always carry a free amino group, m moles of fatty acid or mixture of fatty acids of the indicated kind, where m is an integer from 1 to n, are used per mole of alkylenediamine or poylalkylenepolyamine of the formula (5). Accordingly, there are used for example 1 mole of fatty acid per mole of alkylenediamine, 1 or 2 moles of fatty acid per mole of dialkylenetriamine and 1, 2, 3 or 4 moles of fatty acid per mole of tetraethylenepentamine. Condensates in their preferred embodiment as component (b), from which the sizing agents (A) are obtainable, therefore have the probable formula

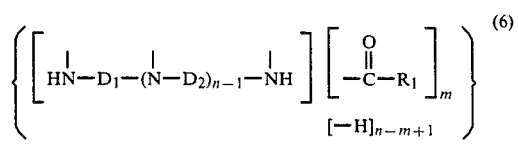

wherein $R_1$ is alkyl or alkenyl, each of 6 to 22, preferably 8 to 22 and, most preferably, 16 to 20 carbon atoms, and $D_1$, $D_2$, m and n have the given meanings.

As a rule, either fatty alcohols or fatty amines or condensates of fatty acids and alkylenediamines or polyalkylenediamines of the indicated kind are used as component (b) from which the sizing agents (A) are obtainable. Also suitable, however, are mixtures of fatty alcohols and fatty amines, of fatty alcohols and condensates of the indicated kind, or of fatty amines and condensates of the indicated kind, or even of fatty alcohols, fatty amines and condensates of the indicated kind.

The novel compounds eligible for use as sizing agent (A) have the probable formula

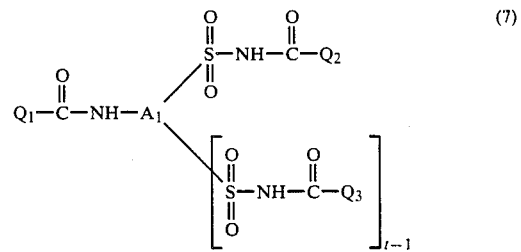

wherein $Q_1$, $Q_2$ and $Q_3$ differ from one another or are preferably identical and are each

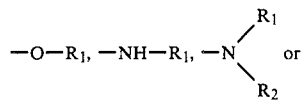

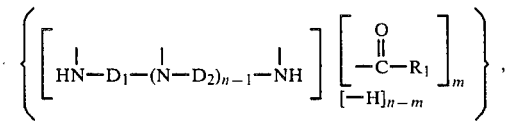

$R_1$ and $R_2$ are different or preferably identical and are each alkyl or alkenyl of 6 to 22, preferably 8 to 22 and, most preferably, 16 to 20 carbon atoms, and $A_1$, $D_1$, $D_2$, n, m and t have the given meanings; or have preferably the probable formula

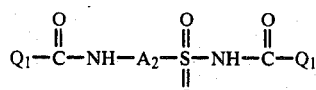 (8)

wherein $Q_1$ is

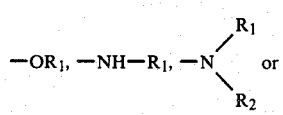

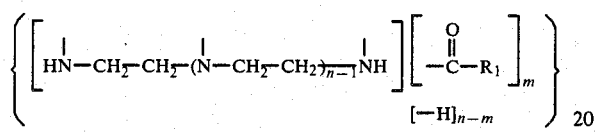

and $A_2$, $R_1$ $R_2$, n and m have the given meanings.

Depending on the meaning of $Q_1$, $Q_2$ and $Q_3$ in formula (7), the novel compounds in which $Q_1$, $Q_2$ and $Q_3$ are identical in their preferred embodiment correspond either to the formula

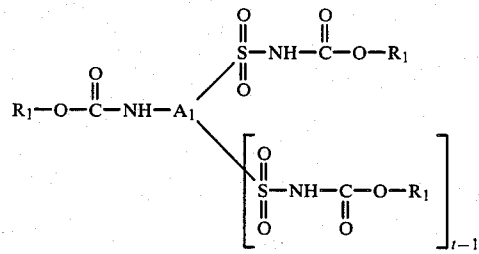 (9)

preferably

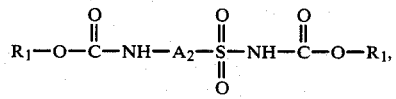 (10)

to the formula

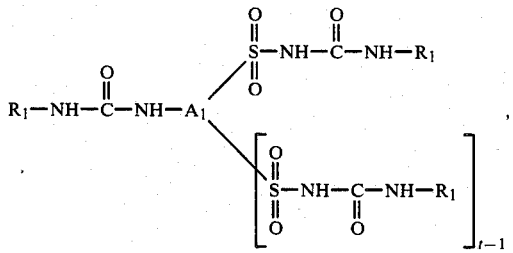 (11)

preferably

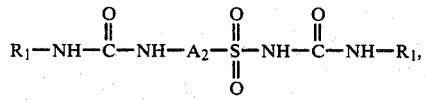 (12)

to the formula

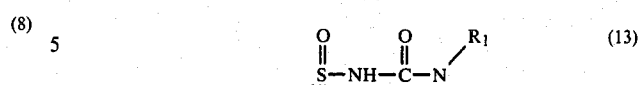 (13)

preferably

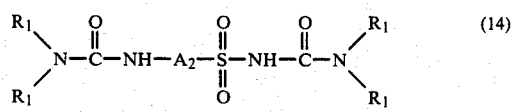 (14)

or to the probable formula

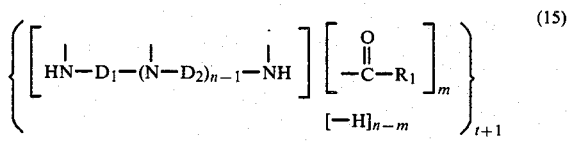 (15)

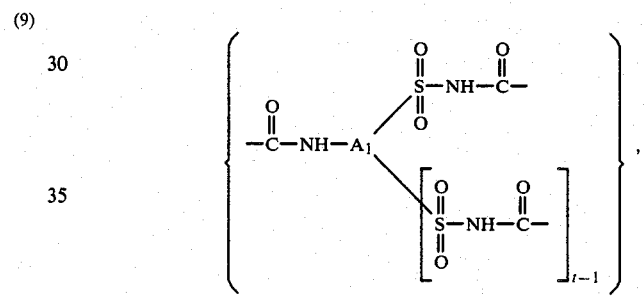

preferably

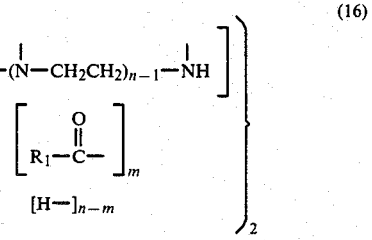 (16)

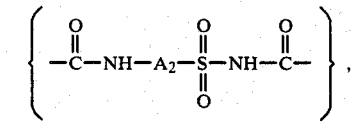

in which $A_1$, $A_2$, $D_1$, $D_2$, $R_1$, $R_2$, n, m and and t have the given meanings.

Specific representatives of particularly interesting novel compounds which are eligible for use as sizing agent (A) are for example those of the formulae

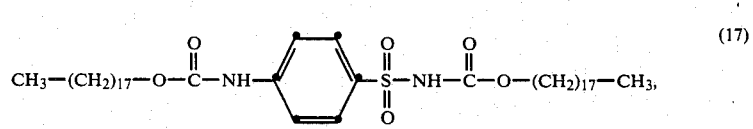 (17)

-continued
 (18)
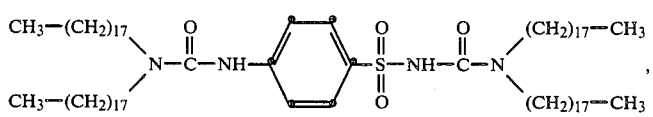 (19)
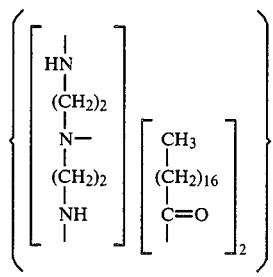 (20)
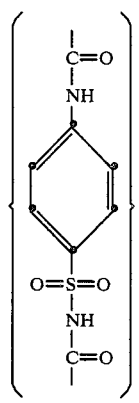
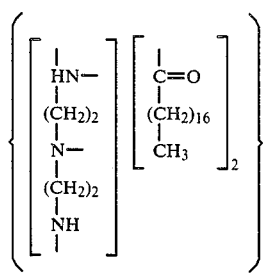
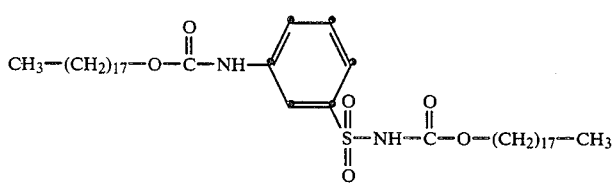 (21)
and
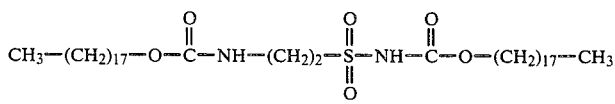 (22)
The process for the preparation of the novel compounds of formula (7) comprises reacting, by methods known per se, 1 mole of the compound of formula (3), with t+1 moles of a fatty alcohol of the formula $$R_1-OH \quad (23)$$

with t+1 moles of a primary or secondary fatty amine of the formula $$R_1-NH_2, \quad (24)$$

or $$R_1-NH-R_2, \quad (25)$$

or with t+1 moles of a condensate of formula (6) from m moles of a fatty acid and 1 mole of an alkylenediamine or polyalkylenepolyamine, where $A_1$, $D_1$, $D_2$, $R_1$, $R_2$, m, n and t have the given meanings. Although it is preferred to react in each case t+1 moles of one of compounds (23), (24), (25) or (6) with 1 mole of the compound of formula (31), it is also possible to react t+1 moles of a mixture of compounds (23), (24), (25) and/or (6).

It is preferred to carry out the reactions of component (a) with component (b) at a maximum temperature of 90° C., preferably in the range from −10° to +60° C., most preferably from 10° to 40° C., normally in the presence of a solvent which must be inert to the starting components and to the final products. Examples of possible solvents are: ethers such as diethyl ether, diisopropyl ether, hydrocarbons or halogenated hydrocarbons, for example dichloroethane, carbon tetrachloride, and also benzene, toluene, chlorobenzene, o-, m- and p-xylene, a technical mixture of xylenes, or also mixtures of the above hydrocarbons. In view of the high reactivity of component (a) with component (b), it is advisable to add component (b) to component (a) for example over the course of ¼ hour to 3 hours, preferably of ½ hour to 1½ hours, the reaction mixture being generally cooled.

After its preparation, the sizing agent normally does not need to be purified, e.g. by recrystallization, before using as component (A) in the paper sizing process of this invention, but can be employed as crude product, i.e. without further processing.

Especially when adding the sizing agent (A) and the retention aid (B) separately (in any order) to the fibre suspension in the process of this invention for sizing paper or cardboard, it is convenient to add the sizing agent partly in salt form. As required, such salts can be prepared by converting the reaction products obtained after the reaction of components (a) and (b) into the corresponding salts, in some cases at least partly, by adding e.g. an alkylamine or alkanolamine containing in all up to 6 carbon atoms, e.g. trimethylamine, triethylamine, monoethanolamine, diethanolamine, preferably by adding potassium hydroxide or, in particular, sodium hydroxide, normally in aqueous medium at room temperature (from about 15° to 25° C.). It is convenient to use an alkali metal hydroxide, e.g. potassium hydroxide or, preferably, sodium hydroxide, or especially ammonia, usually in the form of a dilute aqueous solution (about 1 to 10% by weight). It is advantageous to use generally up to 2 moles, preferably from 0.1 to 1.5 moles and, most preferably, 0.9 to 1.1 moles of ammonia or alkali metal hydroxide per available acid sulfonylcarbonylimide group of the sizing agent. The sizing agents in the form of their salts thus contain acid $-SO_2-NH-CO-$ groups which are at least partly converted into the $-SO_2-N^{\ominus}-CO-M^{\oplus}$ group, wherein $M^{\oplus}$ denotes the corresponding amine, ammoniaum or alkali metal cations.

Preferred sizing agents (A) of the indicated kind have molecular weights of about 200 to 3000, preferably from about 600 to 2000, and, because they contain at least one acid sulfonylcarbonylimide group, have an acid number (mg of KOH/g of substance) or about 15 to 200, preferably of about 25 to 100.

In the paper sizing process of this invention, there is always used—in addition to the novel anionic or acid sizing agent (A)—a polymeric cationic retention aid (B) which normally has a molecular weight of at least 1000, preferably about 2000 to 2 000 000. Retention aids having a molecular weight in the range from 10 000 to 100,000 are particularly preferred. In principle, any commercially available retention aid is suitable for use in the process of this invention. Examples of conventional retention aids (B) which are particularly suitable for use, together with the sizing agent (A), in the process of this invention, are polyalkylenimines, adducts of epihalohydrin with reaction products of polyalkylenepolyamines and aliphatic dicarboxylic acids; adducts of epihalohydrin with reaction products of polyalkylenepolyamines, dicyandiamide and organic dicarboxylic acids which are free or esterified with alkanols; reaction products of dicyandiamide, formaldehyde, ammonium salts of strong inorganic acids and alkylenediamines or polyalkylenepolyamines; cationically modified starches or carbohydrates from carob bean gum or guar gum; copolymers based on polyamide amines and reaction products of epihalohydrins and polymerised diallyl amines.

Preferred adducts of epichlorohydrin with reaction products of polyalkylenepolyamines and aliphatic dicarboxylic acids are described e.g. in British Pat. No. 865,727; adducts of epichlorohydrin with reaction products of dicyandiamide and diethylenetriamine or triethylenetetramine are described e.g. in German "Offenlegungsschrift" No. 2,710,061 and in British Pat. No. 1,125,486; adducts of epichlorohydrin with reaction products of diethylenetriamine, dicyandiamide and dicarboxylic acids which are free or preferably esterified with lower alkanols, in particular dimethyl adipate, are described e.g. in British Pat. No. 1,125,486, and reaction products of dicyandiamide, formaldehyde, ammonium salts of strong inorganic acids and of ethylenediamine or triethylenetetraamine, are described e.g. in U.S. Pat. No. 3,491,064. Preferred cationically modified starches or carbohydrates from carob bean gum or guar gum are adducts of alkylene oxide with these starches or carbohydrates in which the alkylene oxide employed contains 2 or 3 carbon atoms in the alkylene moiety and quaternary ammonium groups. Copolymers based on polyamide amines have molecular weights of $10^3$ to $10^5$, preferably of $10^3$ to $10^4$, and are obtainable e.g. from aliphatic saturated dicarboxylic acids containing 2 to 10 carbon atoms, preferably 3 to 6 carbon atoms, preferably adipic acid, and polyalkylenepolyamines, e.g. polypropylenepolyamine and polyethylenepolyamine, preferably dimethylaminohyroxypropyl diethylenetriamine. They are described e.g. in the CTFA Cosmetic Ingredient Dictionary, 3rd edition 1982 (CFTA=Cosmetic Toiletry and Fragrance Association). Reaction products of epihalohydrins and polymerised diallyl amines preferably have molecular weights of 1000 to 2000 and are described e.g. in U.S. Pat. Nos. 3,700,623 and 4,729,794.

Typical examples of preferred retention aids (B) which are used together with the sizing agents (A) in the paper sizing process of this invention are a maize or potato starch modified with a propylene oxide which contains quaternary ammonium groups, a 25% suspension of which in distilled water at 20° C. has a pH of 4.2 to 4.6, a polyethylenimine having a molecular weight of 10,000 to 100,000, an adduct of epichlorohydrin with a reaction product of triethylenetetraamine and dicyandiamide, an adduct of epichlorohydrin with a reaction product of diethylenetriamine, dicyadiamide and dimethyl adipate, a reaction product of diacyandiamide, formaldehyde, ammonium chloride and ethylenediamine, an adduct of epichlorohydrin with a poly-N-methyl diallyl amine, and a copolymer of adipic acid and dimethylaminohydroxypropyl diethylenetriamine.

In the process of this invention there will normally be used 0.02 to 3, preferably 0.05 to 3 or 0.1 to 3 percent by weight, in particular 0.1 to 0.8 or 0.2 to 0.8 percent by weight of the sizing agent (A), and 0.02 to 3, preferably 0.05 to 3 or 0.1 to 3 percent by weight, in particular 0.1 to 0.4 or 0.2 to 0.4 percent by weight of the retention aid (B), said amounts both being expressed as solids in (A) and (B) and based on the solids content of the fibre suspension. An amount of 0.02 to less than 0.05 percent by weight of the sizing agent (A) and of the retention aid (B) suffices only for the size press control which is not ascertainable by means of conventional sizing tests (q.v. for example the article "Control and understanding of size press pickup" by D. R. Dill in TAPPI Journal Vol. 57, No. 1, of January 1974, pp. 97–100) (TAPPI=Proceedings of The Technical Association of the Pulp and Paper Industry). The fibre suspension to which the sizing agent (A) and the retention aid (B) are added normally has a solids content of 0.1 to 5, preferably 0.3 to 3, most preferably 0.3 to 1 percent by weight, and a Schopper-Riegler freeness of about 10° to 60°, in particular 20° to 60°, preferably 20° to 45° and, most preferably, 25° to 35°. The suspension contains as a rule pulp, especially pulp obtained from coniferous wood, e.g. pinewood, or from hardwood, i.e. deciduous wood, e.g. beechwood, which pulp is prepared by conventional methods, e.g. by the sulfite process or, in particular, the sulfate process. In addition, the fibre suspension may contain groundwood. The fibre suspension can also contain aluminiferous waste paper. Also suitable are pulp suspensions which are prepared by the CMP or CTMP process (chemimechanical and chemithermomechanical pulping processes, q.v. for example the article "Developments in refiner mechanical pulping" by S. A. Collicut and co-workers in TAPPI, Vol. 64, No. 6, of June 1981, pp. 57-61).

The fibre suspension can additionally contain organic or mineral fillers. Suitable organic fillers are e.g. synthetic pigments, for example polycondensates of urea or melamine and formaldehyde which have large specific surface areas, are in highly disperse form and are described e.g. in British Pat. Nos. 1,043,937 and 1,318,244, or mineral fillers such as montmorillonite, titanium dioxide, calcium sulfate and, in particular talcum, kaolin and/or chalk (calcium carbonate). The fibre suspensions contain as a rule 0 to 40, preferably 5 to 25 and, most preferably, 15 to 20 percent by weight of the fillers of the indicated kind expressed as solids, based on the solids content of the fibre suspension.

The pH of the fibre suspension can vary within a wide range, suitable values being e.g. from 3.5 to about 10.

If, for example, calcium carbonate is added, alkaline fibre suspensions with a pH of about 7 to 9, preferably 7.5 to 8.5, are obtained. In the absence of calcium carbonate, it is possible to obtain acid fibre suspensions with a pH of 3.5 to 7, preferably 5 to 7 and, most preferably, 5 to 6, by adding an acid, e.g. sulfuric acid or formic acid or, in particular, a latent acid sulfate such as aluminium sulfate (alum).

Fibre suspensions which contain no filler can be in a wide pH range from e.g. 3.5 to 10. Fibre suspensions are preferred which have a pH of about 7 to 9, optionally by adding chalk, and are advantageous to the extent that possible corrosion in the sensitive paper machines is ruled out.

The fibre suspensions can also contain additives, e.g. starch or its degradation products, which increase the fibre/fibre bond or fibre/filler bond.

It is also possible to add high molecular weight polymers of the acrylic series, e.g. polyacrylamides, with molecular weights of over 1 000 000 to the fibre suspensions as auxiliaries for retaining pulp fibre microparticles. Minimal amounts of about 0.005 to 0.02 percent by weight, expressed as solids in the polymer and based on the solids content of the fibre suspensions, suffice for this purpose.

The fibre suspension is further processed to paper on cardboard in the process of this invention in a manner known per se on sheet formers or, preferably, continuously in paper machines of conventional construction. After drying at about 100° to 140° C. for about ½ minute to 10 minutes, papers having a variable weight per unit area of e.g. 50 to 200 g/m$^2$ are obtained.

As mentioned at the outset, the aqueous composition for carrying out the paper sizing process of this invention contains the sizing agent (A), in addition to optional customary auxiliaries, provided the sizing agent and the retention aid (B) are added separately to the fibre suspension. In this case, the composition contains the sizing agent partly in salt form (obtained by concurrently using e.g. ammonia, an alkylamine or alkanolamine or an alkali metal hydroxide of the indicated kind in the ratios stated above). In general, such compositions contain 5 to 30 percent by weight, preferably 5 to 20 percent by weight of the sizing agent which is partly in salt form expressed as solids, based on the weight of the aqueous composition.

On the other hand, if the sizing agent (A) and the retention aid (B) are added simultaneously to the fibre suspension, the aqueous composition contains, in addition to the optional customary auxiliaries, (A) 2 to 40 percent by weight, preferably 5 to 30 percent by weight and, most preferably, 5 to 10 percent by weight of sizing agent (calculated as solid), based on the weight of the aqueous composition, which sizing agent being optionally in salt form, and (B) 0.1 to 20 percent by weight, preferably 0.5 to 10 percent by weight, most preferably 3 to 8 percent by weight of retention aid (calculated as solid), based on the aqueous composition.

The aqueous compositions of the above kind may contain surface-active compounds as customary auxiliaries, e.g. dispersants or also emulsifiers and/or water-soluble organic solvents. Examples of suitable dispersants and emulsifiers are conventional ligninsulfonates, adducts of ethylene oxide and alkyl phenols, fatty amines, fatty alcohols or fatty acids, fatty acid esters of polyhydric alcohols, substituted benzimidazoles, or condensates of aromatic sulfonic acids and formaldehyde. Further surface-active compounds are preferably anionic surfactants, in particular sulfate surfactants, e.g. diethanolamine lauryl sulfate, or ethoxylated lauryl sulfates. Possible water-soluble organic solvents are aliphatic ethers of 1 to 10 carbon atoms, e.g. dioxan, ethylene glycol n-butyl ether or diethylene glycol monobutyl ether, or alcohols of 1 to 4 carbon atoms, e.g. isopropanol, ethanol or methanol.

The compositions are prepared in conventional manner by stirring the sizing agent (A) together with the retention aid (B), or the sizing agent (A), usually partly in salt form, by itself either in the melt state or preferably in the solid state, in particular in powder form, normally in the presence of glass beads and, if necessary, of an emulsifier (if the sizing agent is in the melt state) or a dispersant (if the sizing agent is in powder form), at a maximum temperature of 90° C., preferably of about 50° to 85° C. if emulsions are prepared, and preferably at about 15° to 25° C. if dispersions are prepared, to give storage stable, homogeneous emulsions or dispersions which can be further diluted. As the sizing agents together with the retention aids, or the sizing agents which are partly in salt form, are usually self-dispersing or self-emulsifying, the use of dispersants or emulsifiers is generally not absolutely necessary. This also applies to the optional use of solvents and/or surfactants, which are employed only if the storage stability of the dispersions or emulsions is insufficient.

An advantage of the process of this invention is that fibre suspensions of widely differing kind can be processed with relatively small amounts of sizing agent and retention aid, in simple manner, to give paper which has good sizing properties (ink flotation time and, in particular, water absorption according to Cobb). The paper which is sized by the process of this invention has good mechanical properties, i.e. good strength, especially good tear strength. A good reproducibility of the process is ensured. In particular, it is possible to process fibre suspensions which contain groundwood or waste paper. The compatibility of the sizing agent employed in the process of the invention with different fillers, e.g. kaolin, and also with other ingredients, e.g. alum, in an acid range of the fibre suspensions, is also advantageous. The sizing agents are also readily compatible with fluorescent whitening agents. In addition, the degree of whiteness of the size paper is not materially influenced by the sizing and may even be improved. In particular, the generally surprisingly good storage stability of the sizing agent dispersions of the indicated kind is very advantageous.

In the following Examples, parts and percentages are by weight.

PREPARATION OF THE NOVEL COMPOUNDS AS SIZING AGENTS

Example 1

270 parts (1 mole) of octadecanol are dissolved in 1200 parts of toluene. To this solution is added a solution of 112 parts (0.5 mole) of 4-isocyanatobenzenesulfonyl isocyanate (0.5 mole) in 500 parts of toluene over 1 hour while keeping the temperature of the reaction mixture between 20° and 25° C. by external cooling. When this addition is complete, the reaction mixture is heated to 50° C. and stirred for 1 hour at this temperature. The toluene is then distilled off from the reaction mixture under reduced pressure, affording 365 parts of the reaction product of formula (17) as a white powder.

For analysis, 1 part of the reaction product is recrystallised from dioxan. The recrystallised product has a melting point of 125°–127° C. and an acid number of 74.

Example 2

The procedure of Example 1 is repeated using 269 parts (1 mole) of octadecylamine instead of 270 parts of octadecanol, to give 362 parts of the reaction product of formula (18) as a white powder. The recrystallised product has a melting point of 159°–166° C. and an acid number of 72.

Example 3

The procedure of Example 1 is repeated using 522 parts of dioctadecylamine (1 mole) instead of 270 parts of octadecanol, to give 603 parts of the reaction product of formula (19) as a white powder. The recrystallised product has a melting point of 92°–95° C. and an acid number of 43.

Example 4

The procedure of Example 1 is repeated using 631 parts of a condensate of 2 moles of stearic acid and 1 mole of diethylenetriamine (1 mole) instead of 270 parts of octadecanol, to give 714 parts of the reaction product of the probable formula (20) as an ochre powder. The crude product has a melting point of 90°–100° C. and an acid number of 39.

Example 5

The procedure of Example 1 is repeated using 112 parts (0.5 mole) of 3-isocyanatobenzenesulfonyl isocyanate instead of 112 parts of 4-isocyanatobenzenesulfonyl isocyanate. 1 part of the crude product is recrystallised from acetone, affording 367 parts of the reaction product of formula (21) as a white powder. After recrystallisation, the product has as melting point of 90°–92° C. and an acid number of 73.

Example 6

The procedure of Example 1 is repeated using 72 parts (0.5 mole) of 2-isocyanato-1-ethanesulfonyl isocyanate instead of 112 parts of 4-isocyanatobenzenesulfonyl isocyanate. 1 part of the crude product is recrystallised from ethyl acetate, affording 326 parts of the reaction product of formula (22) as a white powder. After recrystallisation, the product has a melting point of 53°–54.5° C. and an acid number of 78.

APPLICATION EXAMPLES

Examples 7 to 13

To a fibre suspension which contains bleached birch sulfate pulp and pine sulfate pulp in a weight ratio of 1:1 in water of 10° (German water hardness), and which has a Schopper-Riegler freeness of 35° and a solids content of 0.5%, are added 20% of chalk as filler and then 0.01% of PERCOL 292 ® (cationic high molecular weight (MG>1.10$^7$) polyacrylamide) as auxiliary for retaining pulp fibre microparticles. The pH of the fibre suspension is as indicated in Table I below. The percentages refer to solids in filler and assistant, based on the solids content of the fibre suspension.

Formulations of the sizing agent are prepared by stirring 7% of each of the indicated sizing agents in powder form (obtained as crude product) with 3.5% of POLYMIN P ® (polyethylenimine with a molecular weight of 10,000 to 100,000) as retention aid, in the presence of deionised water and of glass beads having a diameter 2 mm, at room temperature (15° to 25° C.). The dispersions so obtained are pourable, homogeneous and storage stable. The percentages refer to solids in fillers and retention aids, based on the total weight of the formulation.

The aqueous formulation of the sizing agent and the retention aid is added to the fibre suspension in such a manner as to give the amounts of sizing agent indicated in Table I, expressed as solids and based on the solids content of the fibre suspension. The fibre suspension is then processed in a laboratory "Formette Dynamique" sheet former (supplied by Allimand, Grenoble, France) to paper sheets which, after they have been dried at 130° C. for 3 minutes, have a weight per unit area of 80 g/m$^2$.

Both surfaces of the paper sheets so obtained, i.e. the surface obtained on the wire side of the sheet former and the adjacent or top side, are tested for their sizing properties. This is done by measuring the water absorption according to Cobb over 30 seconds (WA Cobb$_{30}$) in accordance with DIN 53 132. The results of the WA Cobb$_{30}$ measurements in g/m$^2$ of the wire side (WS) and top side (TS) after drying at 130° C. and storage for 1 day at 20° C. are reported in Table I. The lower the water absorption, the better the paper sizing. WA Cobb$_{30}$ values above 100 denote a completely unsatisfactory sizing of the paper.

of dicyandiamide and triethylenetetramine which is further reacted with epichlorohydrin and is prepared in accordance with Example 2 of German "Offenlegungsschrift" No. 2,710,061, a reaction product of dicyandiamide, formaldehyde, ammonium chloride and ethylenediamine (prepared in accordance with Example 1 of U.S. Pat. No. 3,491,064), or RETAMINOL K ® (polyethylenimine having a molecular weight of 20 000 to 40 000). Only a poor sizing with Cobb values of about 150 to 200 are obtained by using a sizing agent of any one of Examples 1 to 6 without a retention aid or a retention aid of the aforementioned kind without a sizing agent.

Examples 14 to 19

The procedures of Examples 7 to 13 are repeated, except that the sizing agent and retention aid are added separately to the fibre suspension. The sizing agent (6% or 15%) is stirred, in powder form, at room temperature (15°–25° C.) in the presence of water and glass beads with an aqueous 5% ammonia solution to give a self-emulsifying, pourable and storage stable emulsion of the formulation as indicated in Table II. The val% indicates the number of equivalents of ammonia for 100 equivalents, based on the number of acidic sulfonylcarbonylimide groups contained in the respective sizing agent. The indicated amount of the retention aid POLYMIN P ®, expressed as solids, is added to the fibre suspension 10 seconds after the addition of the indicated amount of sizing agent, expressed as solids, said amounts being based on the solids content of the fibre suspension. The sizing results are also reported in Table II.

TABLE I

| | | | | WA Cobb$_{30}$ (g/m$^2$) | | | |
| | | Amount | | after drying | | after storage for 1 day | |
| Ex. | Sizing agent | (%) | pH of the suspension | WS | TS | WS | TS |
|---|---|---|---|---|---|---|---|
| 7 | reaction product of Example 1 | 0.5 | 8.7 | 18 | 13 | 15 | 10 |
| 8 | reaction product of Example 1 | 0.25 | 8.7 | 16 | 13 | 13 | 11 |
| 9 | reaction product of Example 2 | 0.2 | 8.7 | 17 | 13 | 16 | 12 |
| 10 | reaction product of Example 3 | 0.5 | 8.7 | 17 | 13 | 15 | 11 |
| 11 | reaction product of Example 4 | 0.5 | 8.7 | 19 | 13 | 16 | 11 |
| 12 | reaction product of Example 6 | 0.5 | 8.7 | 19 | 13 | 16 | 12 |
| 13 | reaction product of Example 5 | 0.5 | 8.7 | 20 | 14 | 24 | 14 |

Similar results are obtained by using, as retention aid, CATO 110 ® (cationically modified starch which is modified with a propylene oxide containing ammonium groups; pH of a 25% suspension in distilled water at 20° C.=4.2 to 4.6) instead of POLYMIN P ®, a condensate

TABLE II

| | | | | | | WA Cobb$_{30}$ (g/m$^2$) | | | |
| | | Amount of sizing | Amount of retention- | | pH of the sus- | after drying | | after storage for 1 day | |
| Ex. | Formulation of the sizing agent | agent (%) | aid (%) | Filler | pension | WS | TS | TS | SS |
|---|---|---|---|---|---|---|---|---|---|
| 14 | 6% of the reaction product of Ex. 1 100 val % of ammonia | 0.3 | 0.25 | 20% of chalk | 8.7 | 17 | 14 | 15 | 14 |
| 15 | 15% of the reaction product of Ex. 2 100 val % of ammonia | 0.3 | 0.25 | 20% of chalk | 8.6 | 24 | 15 | 20 | 13 |
| 16 | 15% of the reaction product of Ex. 2 100 val % of ammonia | 0.4 | 0.25 | 20% of chalk | 8.7 | 20 | 14 | 18 | 12 |
| 17 | 15% of the reaction product of Ex. 4 100 val % of ammonia | 0.35 | 0.25 | 20% of chalk | 8.7 | 61 | 26 | 53 | 18 |
| 18 | 6% of the reaction product of Ex. 5 100 val % of ammonia | 0.5 | 0.25 | 20% of chalk | 8.7 | 14 | 13 | 14 | 13 |

TABLE II-continued

| Ex. | Formulation of the sizing agent | Amount of sizing agent (%) | Amount of retention-aid (%) | Filler | pH of the suspension | WA Cobb30 (g/m²) after drying WS | WA Cobb30 (g/m²) after drying TS | WA Cobb30 (g/m²) after storage for 1 day TS | WA Cobb30 (g/m²) after storage for 1 day SS |
|---|---|---|---|---|---|---|---|---|---|
| 19 | 15% of the reaction product of Ex. 6 100 val % of ammonia | 0.5 | 0.25 | 20% of chalk | 8.7 | 17 | 14 | 38 | 26 |

Sizing results analogous to those reported in Table II are obtained by using from 10 to 200 val% of ammonia or sodium hydroxide (as 5% aqueous solutions) for formulating the sizing agent.

Similar results are also obtained by first adding the retention aid to the fibre suspension and subsequently adding the sizing agent 10 seconds later. The same also applies by dispensing with the addition of PERCOL 292 ® and/or of a filler. Similar results are likewise obtained by using talcum or kaolin as filler instead of chalk or by using chalk in the presence of alum. Good sizing results are also obtained by using fibre suspensions which contain groundwood.

What is claimed is:

1. A process for sizing paper or cardboard, which comprises adding to an aqueous cellulose-containing fiber suspension (A) a sizing agent of the formula

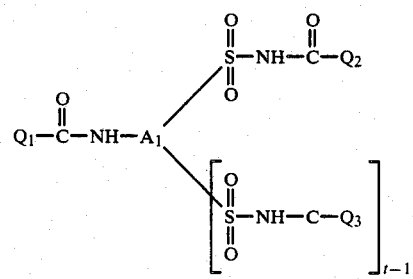

wherein $A_1$ is a divalent or trivalent aliphatic cycloaliphatic or aromatic radical of up to 10 carbon atoms, $Q_1$, $Q_2$ and $Q_3$ are each

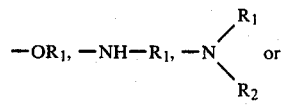

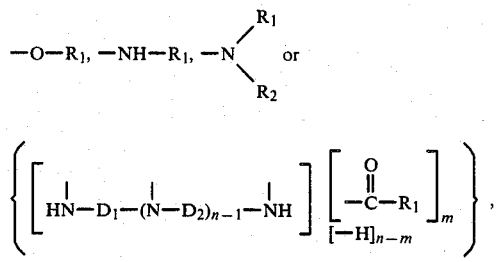

$D_1$ and $D_2$ are each ethylene or propylene, $R_1$ and $R_2$ are each alkyl or alkenyl of 8 to 22 carbon atoms, n is an integer from 1 to 5, t is 1 or 2, and m is an integer from 1 to n, and (B) a polymeric cationic retention aid.

2. A process according to claim 1 in which the fiber suspension additionally contains a filler.

3. A process according to claim 2, which comprises using, as additional filler, a condensate of formaldehyde and urea, titanium dioxide, talcum, kaolin, montmorillonite or chalk.

4. A process according to claim 1, which comprises using, as component (A), a sizing agent of the formula

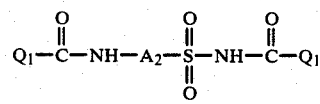

wherein $A_2$ is cycloalkylene, naphthylene, unsubstituted or methyl-substituted phenylene, or alkylene of 2 to 8 carbon atoms, $Q_1$ is

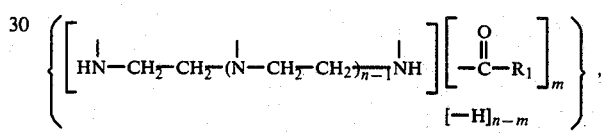

$R_1$ is alkyl or alkenyl of 8 to 22 carbon atoms, n is an integer from 1 to 5 and m is an integer from 1 to n.

5. A process according to claim 1, wherein the sizing agent (A) has an acid number from 15 to 200 and a molecular weight from 300 to 3000.

6. A process according of claim 1, wherein the retention aid (B) has a molecular weight of 1000 to 2 000 000.

7. A process according to claim 1, which comprises using, as retention aid (B), a polyalkylenimine, an adduct of epihalohydrin with a reaction product of a polyalkylenepolyamine and an aliphatic dicarboxylic acid; an adduct of epihalohydrin with a reaction product of a polyalkylenepolyamine, dicyandiamide and an organic dicarboxylic acid which is free or esterified with an alkanol; a reaction product of dicyandiamide, formaldehyde, an ammonium salt of a strong inorganic acid and an alkylenediamine or a polyalkylenepolyamine; a cationically modified starch or carbohydrate from carob bean gum or guar gum; a copolymer based on a polyamide amine or a reaction product of an epihalohydrin and a polymerised diallyl amine.

8. A process according to claim 1, which comprises using 0.02 to 3 percent by weight of the sizing agent (A) and 0.02 to 3 percent by weight of the retention aid (B), both amounts being expressed as solids in (A) and (B) and based on the solids content of the fibre suspension.

9. Paper or cardboard sized by the process according to claim 1.

* * * * *